US00PP33129P3

(12) United States Plant Patent
Klemm et al.

(10) Patent No.: US PP33,129 P3
(45) Date of Patent: Jun. 1, 2021

(54) *CALIBRACHOA* PLANT NAMED 'KLECA18408'

(50) Latin Name: ***Calibrachoa* sp.**
Varietal Denomination: KLECA18408

(71) Applicant: Klemm+Sohn GmbH & Co. KG, Stuttgart (DE)

(72) Inventors: Nils Klemm, Stuttgart (DE); Anita Stöver, Ostfildern (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 16/870,998

(22) Filed: May 10, 2020

(65) Prior Publication Data

US 2020/0383255 P1 Dec. 3, 2020

Related U.S. Application Data

(60) Provisional application No. 62/921,069, filed on May 29, 2019.

(51) Int. Cl.
*A01H 5/02* (2018.01)
*A01H 6/82* (2018.01)

(52) U.S. Cl.
USPC ..... Plt./413
CPC ..... *A01H 6/821* (2018.05); *A01H 5/02* (2013.01)

(58) Field of Classification Search
USPC ..... Plt./413
CPC ... A01H 5/02; A01H 5/12; A01H 5/00; A01H 6/82; A01H 6/821; A01H 6/14
See application file for complete search history.

(56) References Cited

PUBLICATIONS

Ball Seed Minifamous Neo Violet Ice, retrieved onOct. 19, 2020, retrieved from the Internet at https://www.ballseed.com/PlantInfo/?phid=066007160004397, one page. (Year: 2020).*
Ball Seed Highlights from 2019 California Spring Trials, retrieved on Oct. 19, 2020, retrieved from the Internet at file:///C:/Users/jhwu/Downloads/19006_BSC_NV_CAST_book_LR.pdf, 3 intro pages, 19. (Year: 2019).*
Wright Floriculture's Finest Plant Varieties Coming Soon to California Spring Trials 2019, retrieved from the Internet at https://www.greenhousegrower.com/crops/floricultures-finest-plant-varieties-coming-soon-to-california-spring-trials-2019/, 8 pp. (Year: 2019).*

* cited by examiner

*Primary Examiner* — June Hwu
(74) *Attorney, Agent, or Firm* — Weatherly IP Solutions, LLC; Barbara Campbell

(57) ABSTRACT

A new *Calibrachoa* plant designated 'KLECA18408' particularly distinguished by light orange and red bicolored flowers, is disclosed.

1 Drawing Sheet

Genus and species: *Calibrachoa* sp.
Variety denomination: 'KLECA18408'.

BACKGROUND OF THE NEW PLANT

The present invention comprises a new and distinct variety of *Calibrachoa*, botanically known as *Calibrachoa* sp., and hereinafter referred to by the variety name 'KLECA18408'. 'KLECA18408' originated from a controlled cross conducted in August 2014 in Stuttgart, Germany, between the female *Calibrachoa* 'USCAL08501' (U.S. Plant Pat. No. 24,503), also commercially known as SUPERBELLS 'Pomegranate Punch' and the proprietary male *Calibrachoa* 'CA-2013-0284' (not patented).

'KLECA18408' has been found to reproduce true to type in successive generations of asexual propagation in Stuttgart, Germany via vegetative stem cuttings.

SUMMARY

The following are the most outstanding and distinguishing characteristics of 'KLECA18408' when grown under normal horticultural practices in Stuttgart, Germany.

1. Light orange and red bicolored flowers; and
2. A semi-upright habit.

DESCRIPTION OF THE PHOTOGRAPH

This new *Calibrachoa* plant is illustrated by the accompanying photograph of a plant grown outdoors in Stuttgart, Germany. The photograph shows the whole plant, unless otherwise noted, including the flowers and foliage and buds. The colors shown are as true as can be reasonably obtained by conventional photographic procedures. The photograph is of a whole plant photo of 'KLECA18408' 12-weeks-old, taken in January 2019.

DESCRIPTION OF THE NEW VARIETY

The following detailed descriptions set forth the distinctive characteristics of 'KLECA18408'. The data which define these characteristics were collected from asexual reproductions carried out in Stuttgart, Germany. Data was collected on plants grown 18 weeks since potting in a greenhouse with no pinching or growth regulators. Color references are to The R.H.S. Colour Chart of The Royal Horticultural Society of London (R.H.S.), $5^{th}$ edition (2007).

Classification:
*Family*.—Solanaceae.
*Botanical*.—*Calibrachoa* sp.
*Designation*.—'KLECA18408'.
Parentage:
*Female parent*.—'USCAL08501' (U.S. Plant Pat. No. 24,503), also commercially known as SUPERBELLS 'Pomegranate Punch'.
*Male parent*.—'CA-2013-0284' (unpatented).
Plant:
*Life cycle*.—Annual.
*Form*.—Short-lived subshrub.
*Habit*.—Semi-upright.
*Height* (*from soil line to top of foliage*).—17 cm.
*Spread*.—44 cm.
*Propagation*.—Vegetative.
*Type cuttings*.—Tip cuttings.
*Time to produce a rooted cutting*.—3 weeks.
*Disease and pest resistance/susceptibility*.—To date, plants of 'KLECA18408' have not been observed to be resistant or susceptible to pathogens and pests common to *Calibrachoa* plants.
Stems:
*Stem color*.—RHS 143C.
*Pubescence*.—Present.
*Pubescence color*.—RHS 155A.
*Stem diameter*.—0.2 cm.
*Stem length*.—From soil line to first node: 1.5 cm. Total length: 27 cm.
*Internode length*.—1.7 cm.
Foliage:
*Arrangement*.—Opposite.
*Shape*.—Acute.
*Apex*.—Broadly acute.
*Base*.—Attenuate.
*Margin*.—Entire.
*Surface*.—Moderately glandular pubescent.
*Surface pubescence*.—Present.
*Pubescence color*.—RHS 155A.
*Venation*.—Arcuate.
*Venation color*.—Upper surface: RHS 144A. Lower surface: RHS 145B.
*Length*.—4.2 cm.
*Width*.—1.4 cm.
*Color*.—Upper surface: RHS 137A. Lower surface: RHS 138B.
*Fragrance*.—Absent.
Inflorescence:
*Flowering habit*.—Single flowers.
*Flower type*.—Determinate inflorescence.
*Flowering requirements*.—A minimum of light sun is required.
*Duration of flowers*.—6 days.
*Shape*.—Funnel form.
*Lobing of the flower*.—Weak.
*Conspicuousness of the corolla veins* (*both inner and outer*).—Weak.
*Fragrance*.—Absent.
*Flower depth*.—2.2 cm.
*Flower tube length*.—1.7 cm.
*Flower tube diameter*.—0.6 cm.
*Flower diameter*.—4.9 cm.
*Calyx*.—Funnel shaped, salverform.
Inflorescence bud:
*Surface*.—Smooth.
*Length*.—2.4 cm.
*Diameter*.—0.5 cm.
*Shape*.—Elliptic.
*Color*.—RHS 52C (limbs) and RHS 154B (throat).
Peduncles:
*Length*.—1.7 to 2.0 cm.
*Diameter*.—0.1 cm.
*Color*.—RHS 144B.
*Texture*.—Densely glandular pubescent.
*Anthocyanin color*.—Absent.
Sepals:
*Shape*.—Lanceolate.
*Apex*.—Narrowly acute.
*Margin*.—Entire.
*Length*.—1.4 cm.
*Diameter*.—0.3 cm.
*Sepal color*.—Upper surface: RHS 137A. Lower surface: RHS 137C.
Petals:
*Shape*.—Obcordate.
*Length*.—2.2 cm.
*Apex*.—Truncate.
*Margin*.—Entire.
*Base*.—Fused in the tube.
*Texture, upper surface*.—Glabrous.
*Texture, lower surface*.—Glandular pubescent, dense along venation.
*Lobe length*.—2.2 cm.
*Lobe width*.—2.2 cm.
*Color*.—Lobe color: Upper surface: RHS 30A towards the apex and a large transition of RHS 187A towards the base of the corolla lobe. Lower surface: RHS 48C. Corolla tube color: Inner: RHS 15A. Outer: RHS 154B. Immature and fading colors: No difference from the colors of mature flower.
*Fragrance*.—Absent.
Reproductive organs:
*Stamen number*.—5.
*Anther color*.—RHS 13A.
*Filament color*.—RHS 1C.
*Pollen color*.—RHS 8B.
*Placenta arrangement*.—Ovate.
*Pistil number*.—1.
*Pistil length*.—0.7 cm.
*Stigma color*.—RHS 144C.
*Style length*.—0.8 cm.
*Style color*.—RHS 144C.
Fruit and seed set: No fruit or seed set observed.

COMPARISON OF 'KLECA18408' WITH PARENTAL LINES AND KNOWN VARIETY

'KLECA18408' is distinguished from the parental lines as follows. Whereas 'KLECA18408' has light orange flowers with a large red transition color to the corolla tube, the female parent 'USCAL08501' has red flowers with a large black transition to the corolla tube, and the male parent 'CA-2013-0284' has yellow-orange flowers with a large red transition color at the corolla tube.

'KLECA18408' can be compared to the commercial *Calibrachoa* variety 'KLECA17020' (unpatented), also commercially known as MINIFAMOUS Neo 'Apricot Strike'. Whereas 'KLECA18408' has a main lobe color of RHS 30A, 'KLECA17020' has a main lobe color of RHS 25C.

We claim:

1. A new and distinct variety of *Calibrachoa* plant designated 'KLECA18408' as illustrated and described herein.

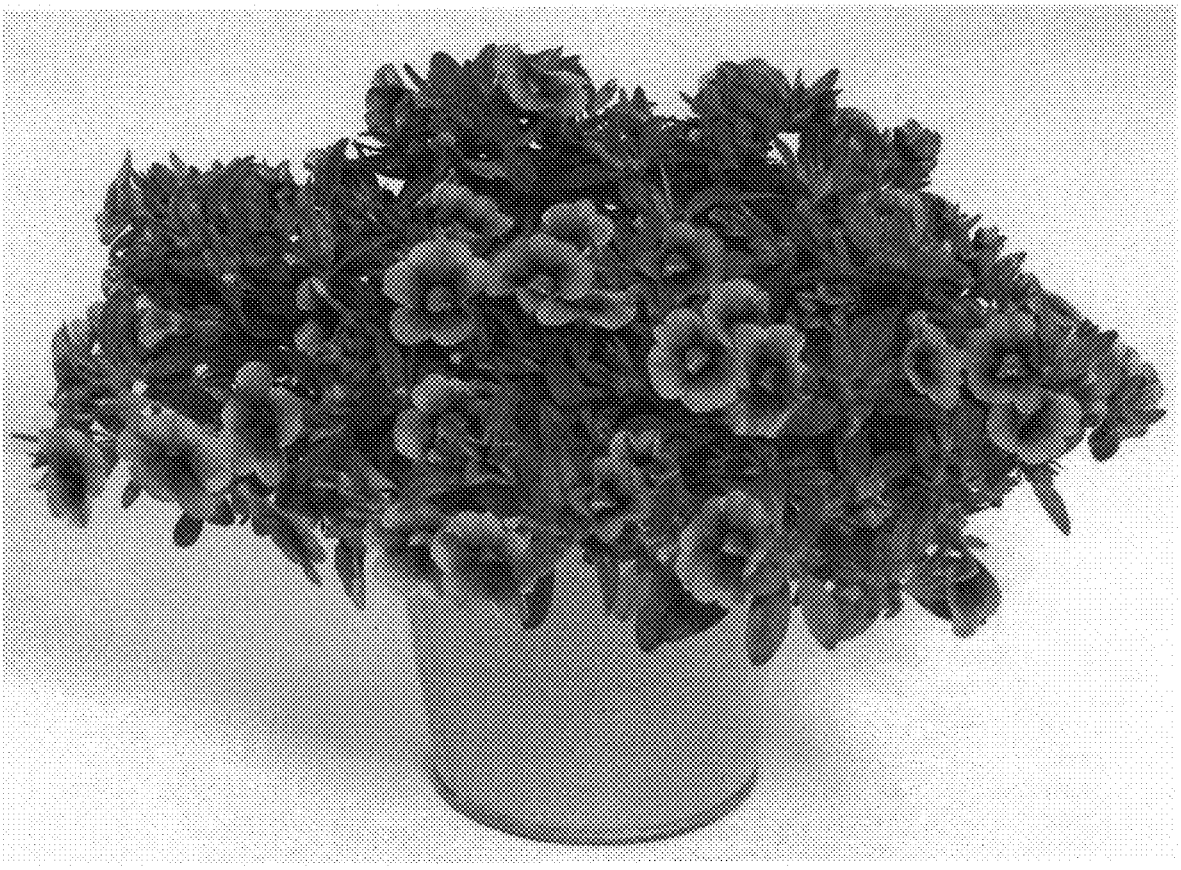

* * * * *